United States Patent [19]
Cox et al.

[11] Patent Number: 5,609,863
[45] Date of Patent: Mar. 11, 1997

[54] GLYOXAL COMPOSITION FOR REDUCTION OF ANIMAL WASTE STENCH AND SEPTICITY, AND METHOD THEREOF

[76] Inventors: James P. Cox; Robert W. D. Cox, both of 246 E. Bartlett Rd., Lynden, Wash. 98264

[21] Appl. No.: 509,334

[22] Filed: Jul. 31, 1995

Related U.S. Application Data

[63] Continuation of Ser. No. 155,808, Nov. 22, 1993, abandoned.

[51] Int. Cl.⁶ .................................. A61L 11/00
[52] U.S. Cl. .................. 424/76.6; 424/76.5; 424/76.8
[58] Field of Search ............... 512/4; 424/76.4–76.8, 424/405

[56] References Cited

U.S. PATENT DOCUMENTS

| | | | |
|---|---|---|---|
| 3,446,733 | 5/1969 | Shell | 210/59 |
| 3,505,217 | 4/1970 | Morico | 210/59 |
| 3,843,545 | 10/1974 | Heuston | 252/181 |
| 4,364,835 | 12/1982 | Cheh | 210/752 |
| 4,385,996 | 5/1983 | McCarthy | 210/719 |
| 4,517,369 | 5/1985 | Marinak | 546/345 |
| 4,666,610 | 5/1987 | Kuhns | 210/749 |
| 4,894,452 | 1/1990 | Stephan | 544/192 |

FOREIGN PATENT DOCUMENTS

| | | |
|---|---|---|
| 0212837 | 3/1987 | European Pat. Off. . |
| 2623717 | 6/1989 | France . |
| 8010051 | 1/1983 | Japan . |
| 0040057 | 3/1985 | Japan . |
| 3249565 | 10/1988 | Japan . |
| 1-070062 | 3/1989 | Japan . |
| 2-074259 | 3/1990 | Japan . |
| 823311 | 4/1979 | U.S.S.R. . |
| 1152388 | 5/1969 | United Kingdom . |

OTHER PUBLICATIONS

Nelson Herwig, Toxic Chloramine Induced Intravascular Hemolytic Anemia In Fish, published prior to 1985.
George C. Blaslola, "Chloramines", Pet Age, Jul. 1984.
George R. Helz and Lynn Kosak–Channing, "Dechlorination of Wastewater and Cooling Water", Environ. Sci. Technol., vol. 18, No. 2, 1984.
Dechlorination (brochure), Allied Chemical Corporation, New Jersey, copyright 1977.
Fredrick Warner Wheaton, Aquacultural Engineering, pp. 608–612, 1977.
Morrison & Boyd, Organic Chemistry, pp. 639–641, 1966.
J. Frederic Walker, Formaldehyde, Reinhold Publishing Corporation, New York, 1944.
Non–Formaldehyde Products brochure, "Conquer", J&J publication date unknown.

*Primary Examiner*—Neil S. Levy

[57] ABSTRACT

A composition and method for reducing odor and septicity from animal waste consisting of glyoxal is disclosed. One or more aldehydes can optionally be added to the glyoxal. The aldehydes are selected from the group consisting of benzaldehyde, glycollic aldehyde, acetaldehyde, cinnamaldehyde, salicylaldehyde, citral and propionaldehyde.

Most preferably, the aldehyde is benzaldehyde or citral. The preferred amounts are between about 0.1 percent and super saturation of glyoxal, and between about 5 percent and about 10 percent benzaldehyde and/or citral. The most preferred amounts are about 40 percent glyoxal and about 10 percent benzaldehyde and/or citral.

One or more ketones can optionally be added to the glyoxal. The ketones are selected from the group consisting of diacetyl, ionone, acetylacetone, 3-buten-2-one, mesityl oxide, acetone, methyl ethyl ketone, diethyl ketone, pseudoionone, methyl nonyl ketone, ethyl octyl ketone, propyl heptyl ketone, butyl hexyl ketone, diamyl ketone, acetophenone, benzophenone and dipropyl ketone.

Surfactants and/or metals can also be added to the composition.

3 Claims, No Drawings

5,609,863

GLYOXAL COMPOSITION FOR REDUCTION OF ANIMAL WASTE STENCH AND SEPTICITY, AND METHOD THEREOF

This application is a continuation of application Ser. No. 08/155,808, filed Nov. 22, 1993, now abandoned, the benefit of the filing dates of which are hereby claimed under 35 USC 120.

BACKGROUND OF THE INVENTION

The present invention pertains to treating animal, including human, waste to reduce stench and septicity. More specifically, the present invention is for highly effective, safety improved chemical compositions and methods for treating body wastes to reduce stench and septicity which can replace certain aldehydes.

Aldehydes are known to be effective primary treating aids, but exhibit significant degrees of toxicity in the free state, rendering them unsafe for handling and use. Formaldehyde and glutaraldehyde have long been known to be effective body waste treating aldehydes for reducing stench and septicity. Both are toxic aldehydes existing under all ambient conditions in both liquid and volatile form. The vapors from both aldehydes are toxic to life upon ingestion, contact, and when breathed. Depending upon concentrations and means of contact, injuries can range from dermatitis to death.

Body wastes from humans and other animals are comprised of biochemicals formed with, from, and of food created as a result of food consumption and consequent metabolic activities. Body wastes are essentially of 4 types: Glandular by-products, respiratory by-products, alimentary by-products and water balance by-products.

The present invention is specifically concerned with compositions and methods for reducing stench and septicity of fecal and urinary wastes from human beings and other animals. Compositions and methods for controlling stench and septicity for glandular and respiratory by-products are anticipated only inasmuch as they might occur with primary body wastes comprised of fecal and urinary excreta. Among other matter, fecal and urinary wastes include products of reacted digestive matter such as acids, enzymes and digested foods (digestive liquids and solids), varied microbiological species and their metabolites, volatiles and, sometimes, parasites and disease related matter.

Moreover, facilities utilized by persons to void wastes such as portable, ship, recreational vehicle, and commercial air transportation waste facilities are comprised of tightly sealed and small spaces which tend to easily become polluted with volatiles from collected wastes. This exposure is unhealthy for those who must use such facilities. Many products used today to reduce exposure to this unhealthy environment may accomplish substantial reductions in the typically uncontrolled pollutants. Unfortunately, the toxic nature of these products presents a significant danger to maintenance and other persons exposed to the products of equal or greater threat to health than the pollutants.

Due to the highly unpleasant nature of body waste products and their inherent malaesthetics and pathological potential, many workers have sought to find ways and means to effectively reduce or eliminate stench and/or septicity associated with them.

Indeed a variety of means have been developed both municipally and for specific dwellings which are more or less effective for controlling these wastes safely. In these instances plumbing is the major control feature. Plumbing permits the safe transport of such materials, including the associated volatiles, to central points of specialized processing where the material is stabilized and disposed. Municipal sewage processing, septic tanks and drain fields are examples of these facilities. Few, if any, persons related to the disposal of those specific body wastes are consequently ever exposed to the health hazards of those who use portable body waste receiving and containment facilities.

Many conditions exist where there is increased human exposure to wastes resulting through the necessity for handling or transferring body wastes such as from septic tanks and portable toilets, and such as those common to transportation, marine and recreational vehicles, and construction and event sites. The immediate environment of use for such systems is often noxious and highly unpleasant: for example, a publicly used portable toilet as found at camp grounds. Another problem is spills made during handling and transfers.

Many examples of prior art demonstrating an awareness and effort to resolve one aspect or another of the problems inherent to conditions described are known and are, in many cases, still in use.

Septicity as referred to in the present invention is the presence in body wastes of indigenous forms of fermenting and non fermenting organisms and microorganisms (both hereinafter referred to as microorganisms). These microorganisms constitute the basis of one of the ongoing major pathways of putrefaction or decomposition of body wastes. Many of these, along with infectious microorganism related to specific diseases or disease states, comprise the wide and diverse variety of pathogens which are to be found in association with body wastes. Parasites and other pathogens are encompassed by the term septicity as employed hereinafter.

Stench as referred to in the present invention relates to an unpleasant phenomenon associated with fecal and urinary body wastes, polluted air comprised of two characteristics simultaneously perceived but related to separate, distinct physical events; one of which is olfactory and the other of which is a trigeminal nerve response. The distinction, while little known and seldom differentiated even technically, is significant. As a rule, stench is a considerably more significant occurrence than just odor since, by definition, it is constituted of both an odor (usually but not always malodor) component and a highly reactive (as evidenced by pain) volatile chemical component. In general, odor volatiles per se may be characterized as pleasant or unpleasant, highly distinct, and perceivable in extremely low ranges of concentration. Moreover odor volatiles frequently do not exhibit any threshold of pain, regardless of the concentration. Many volatile molecules do possess both a pure odor character and a trigeminal factor. Trigeminally mediated volatiles are almost always highly reactive, usually polar, molecules which are perceivable in higher concentration ranges and which demonstrate a narrow difference, if any, between threshold of recognition and threshold of pain. Vanillin is an example of a odor molecule, amyl acetate of a composite odor/trigeminal molecule, and ammonia a trigeminal molecule.

Technically speaking ammonia (representing the simplest form of N R'; the principal molecule and moiety specie of body waste decomposition volatiles) is probably not an odor at all.i.e., it is sensed as a trigeminal response and not integrated via the olfactory mucosa to the rhinencephalon. Perception of ammonia is painful because ammonia, and many moieties of it, are destructive to the 5th cranial nerve which reports to the medulla oblongata, and is also destructive to mucosal and other tissues, such as the eyes.

Formaldehyde has long been used as a direct additive to body wastes. Formaldehyde is a very good sterilant and bactericide used within its limitations. Formaldehyde is known to be a very poor penetrant of biological matter and is consequently of somewhat questionable value as a microbicide under many conditions.

Formaldehyde (HCHO) is commercially offered as a 37% to 50% aqueous solution. Its properties: Strong pungent odor, yap d 1,067 (ait=1.000), at −20/4C yap d 0.815, bp −19C. It is a lachrymator, carcinogen, toxic by inhalation, and strong irritant. Threshold limit value (TLV): 1 ppm in air. $LD_{50}$ orally in rats: 0.80 g/kg. Vapors are intensely irritating to mucous membranes. Skin contact may produce irritant dermatitis.

With *Pseudomonas putida*, the threshold concentration for toxicity of formaldehyde was determined in a cell multiplication inhibition test resulting in $EC_{10}$=14 mg/l after 16 hours' exposure. The test was performed with a 35% water dilution. Experiments with *Pseudomonas fluoreszenz* gave a threshold concentration for toxicity of 2 mg/l and 14 mg/l (inhibition of glucose degradation, inhibition of cell multiplication, 16 to 24 hour exposure). Under the same conditions, the threshold concentration for *Escherichia coli* was 1 mg/l. The respiration of activated sludge was not affected by formaldehyde up to 1,995 mg/l (highest test concentration) after 30 minutes' exposure.

Formaldehyde also exhibits significant activity with respect to reduction of stench from body wastes. Despite formaldehyde's poor penetrating qualities, it is effective against stench by both physical and volatile-to-volatile contact. Body waste stench treated with formaldehyde is dramatically, but not entirely, reduced. There are always characteristic, residual qualities of stench which seem unamenable to reduction by formaldehyde. This may not, but probably does, relate to the same functional characteristics which make formaldehyde a poor penetrant of body waste matter; i.e., it lacks adequate solventizing qualities to provide for adequate contact with microbes and stenchophoric elements inherent in the wastes. Formaldehyde reacts poorly, if at all, against lipidaceous moieties of any type. This includes those portions of protein breakdown products which contain lipids or carboxylic groups, as well as lipids per se, associated with body wastes. Upon the oxidative and enzymatic breakdown of lipids, fatty acids, which represent a very strong class of stench molecules, will be released. Also, many amines contain carboxylic groups which become freed with ammonia, or in association with amino nitrogen and sometimes sulfur volatiles, as nitrogen/fatty acid and nitrogen/sulfur/fatty acid complexes. These classes of stench molecules represent the majority of those associated with the decomposition of most protein/lipid containing biowastes, such as body wastes. Formaldehyde is not effective against lipids or fatty acids or fatty acid complexes. In liquid, solid or volatile form it is not lipid soluble and is not effective against these stench volatiles. Used alone, formaldehyde cannot fully meet the objects of the present invention, stench prevention or reliable reduction of septicity.

Despite the above limitations, for a great many years formaldehyde has been used with moderate effect in one form or another for purposes of reducing stench and septicity of body wastes. Chemical product reviews driven by environmental and health safety concerns over the past several decades have, however, made it clear that formaldehyde is a carcinogen. Its vapors are irritating and while long known to be toxic to human life, it is now also known to be a carcinogen. This, of course, does not mean that formaldehyde cannot, or should not, be used under any circumstances, but that uses should be altered to conform with that awareness of its toxic and carcinogenic nature, or alternatives should be sought. Any treatment for body wastes that would be likely to result in persons being exposed to fugitive formaldehyde volatiles should not be used. This is most particularly true where the fugitive formaldehyde could be trapped in an enclosed environment, such as a portable toilet module, recreational vehicle and the like, where human beings will be certain to visit. Moreover, it should not be used even when the fugitive formaldehyde is not likely to be concentrated, such as where a user, worker or other person may be chronically exposed. For example when septic tanks are pumped, portable toilets are emptied, or marine or recreational vehicles are used or when formaldehyde liquids are openly poured into body waste receptacles.

One of many possible examples of common past use which should no longer be allowed is the use of formaldehyde containing solutions in portable toilets. Since the portable toilet is a repository for body wastes of given capacity, a charge of formaldehyde-containing agent is made which is adequate to control that capacity. This, of course, means that if the treatment dose to reduce stench over the capacity cycle has been calculated accurately, there will at all points in time be fugitive formaldehyde volatiles in the portable toilet until the instant capacity has been achieved when, presumably, there would be equilibrium between body waste stench and formaldehyde. The problem is, of course, that proper treatment of a portable toilet to prevent stench means that every single person using the portable toilet saved from the malaesthetics of stench is guaranteed some exposure to formaldehyde vapors. Moreover workers who clean, transport and maintain such equipment can be chronically exposed during formaldehyde handling, make up and treatment, walk-in testing and inspection, and upon clean-up and disposal cycles.

In recent years many manufacturers of products for use with body wastes, being aware of the problems with formaldehyde, have gone to glutaraldehyde as an alternative. While glutaraldehyde does have the advantage of a lower vapor pressure, and is considered somewhat less toxic than formaldehyde, it still suffers from all of the same disadvantages of formaldehyde.

Glutaraldehyde ($C_5H_8O_2$) has a vapor pressure of 17 mm (20C) and liq. density of d 0.72. It is an irritant and carcinogen. TLV ceiling is 0.2 ppm in air. $LD_{50}$ of 25% solution orally in rats: 2.38 ml/kg; by skin penetration in rabbits: 2.56 ml/kg.

Addition of formaldehyde and glutaraldehyde to body wastes can result in some reduction of stench. The mixture can react volatile to volatile with amino nitrogens and freed ammonia. Employed under conditions of high moisture and mechanical agitation, the mixture can influence substantially the reduction of ongoing stench from microbial and indigenous digestive activities upon body wastes. If agitated adequately with body wastes, formaldehyde is not only a powerful microbicide but also can arrest the decomposition of proteins and all species of protein breakdown products, including amino acids. The form of reaction involves strong cross bonding as well as other reactions with proteins and derivative products including peptides, amino acids, urea nitrogen and ammonia. The bonds are strong and resistant to decomposition, so stability can be quite good. Despite its deficiencies, used singularly formaldehyde has been, and would remain, a powerful basic control agent for combined stench and septicity control of body and other bioorganic wastes where proteins and protein products are prominent. Unfortunately, the on-going use of either formaldehyde of glutaraldehyde cannot be justified and should not be continued in view of its significant and clear threat to human health.

Quats can be useful for cleaning septic body wastes from surfaces and consequently may be employed advantageously, as may other surfactants and microbicides, in an accessory capacity to methods and products of the present invention. Quaternary ammonium products (quats) have long been used as surfactants of choice for cleaning biological wastes of all sorts and varieties, including body wastes. For controlling stench and septicity, they are inadequate and impractical under the necessary use conditions discussed herein. Quats and other cationics are insufficiently concentrated for the uses discussed herein. The stench-controlling factor associated with quats is not related to direct action with stench volatiles or even non-volatile stench precursor molecules. Quats act only on contact and not volatile-to-volatile, so they cannot react at all with stench molecules already present.

Two pathways of stench formation from ongoing breakdown of food molecules exist. Components of foodstuffs, such as polypeptides and amines, serve as reservoirs of $NH_3$ and sulfur molecule moieties which, when released through breakdown, form the bulk of fundamental volatiles associated with ongoing generation of body waste stench. One path whereby stench is generated from components such as amines, for example, is due to on-going decompositional effects of digestive factors incorporated during transit through the body, such as enzymes, acids, and microbes. The other path is continued decomposition with generation of stench by-products of metabolites resulting from active fermentation by indigenous and exogenous microbes.

In relatively high concentrations, and when intermixed with body wastes and adequate water as occurs during washing, quats can indirectly reduce stench by killing many of the microbes, and thereby reduce stench volatiles associated with that pathway of stench formation. Reduction of the microbes is equivalent to reduction in septicity.

Quats do not react directly with stench volatiles and do not prevent enzymatic or digestive acid decomposition. In high enough concentrations, quats can effectively reduce microbial populations which generate stench and are septic. However, quats are not effective under typical concentrations in use and conditions of use within the field of the present invention. For example, the addition of an equivalent measure of quats to formaldehyde in a portable toilet would reduce none of the volatiles associated with incoming body wastes, they would not react with stench molecules diffusing over time from the body wastes, they would at best represent only minimal, if any, effect or not prevent any measurable ongoing decompositionally generated stench molecules derived from ongoing artifactual digests, they would not prevent the continued diffusion through the body wastes of those stench molecules, and they would not achieve adequate contact without mechanical agitation with microbes underneath superficial body waste layers to prevent increased septicity and stench generated therefrom.

In short, the addition of quats under these typical conditions and circumstances would do little to reduce or prevent the formation of stench or septicity of body wastes. Under the given circumstances, quats are less able to penetrate than formaldehyde since they exhibit no significant vapor gradient effectiveness against stench molecules, microbes, fermentation metabolites, artifactual digests or byproducts from their ongoing activities. Provided adequate quantities are used to clean body wastes with other conditions being present such as copious water and mechanical agitation to provide contact and emulsification with body wastes, quats can achieve a small degree of effectiveness to control stench by indirectly preventing its formation from microbial fermentation. In conjunction with application under appropriate conditions, the concentration of quats to body waste determines effectiveness; and to the degree that microbes are killed, septicity and (up to a point) stench are reduced accordingly. Quats can be useful for cleaning septic body wastes from surfaces and consequently may be employed advantageously, as may other surfactants and microbicides, in an accessory capacity to methods and products of the present invention.

Added to body wastes, different metals can positively influence them both in terms of reduction of stench and septicity. As is well known, however, many metals are either toxic or undesirable additions even to body wastes due to environmental and public health concerns. Those of particular effectiveness for reducing stench and septicity are cations of all transition metals (with particular reference to copper, cobalt, molybdenum and iron) and the non transition metals (zinc, and to a much lesser degree, aluminum). At least one non-metal which under some circumstances acts similarly to the metals is boron, usually in the form of borax. All other effective metals are either too toxic or too rare for practical use based on current beliefs and availability. Soluble salts of those metals mentioned, however, are convenient products for treating body wastes.

The effects of metals added to body wastes in terms of stench reduction are incomplete, i.e., substantial stench remains which is unamenable to metal treatment. For example, iron in the form of iron sulfate does reduce the overall stench of raw sewage; however a significant portion remains. The remaining stench portion is different, having taken on a somewhat sweet, earthy, but still unpleasant, character. This is also true of zinc, copper and other metals when added to sewage and similar biologic substrates. These metals are thus inadequate treatments to eliminate the stench associated with most biologic substrates, including sewage.

Metals also suffer the same shortcoming as quats in terms of both possessing no vapor-to-vapor reactivity with stench that already exists in association with the substrate, and poor penetration without good mechanical agitation in a high water solvent solution. Metals can be effective microbicides but are usually considerably most effective against fungi and algae in terms of concentrations required to kill than they are against bacteria or viruses. In fact, little is known about the ability of metals per se with respect to affect on viruses. Against bacteria, much higher concentrations are required and some bacteria are more tolerant than others against the effects of metals. It is most probable that, to some extent, the killing ability of a metal is as much related to the nature of the salt or complex from which it is derived. The salt or complex may cause high or low pH's which can be instrumental in causing substantial and, if high or low enough, even total, microbial kills.

Metals in any combination are inadequate to control stench of most biological substrates including body wastes, and they play a limited role in prevention of stench generated from fermentation or from ongoing indigenous digestive generation of stench. At best metals can play only a very limited, if any, practical role in controlling or reducing septicity or prevention of ongoing generation of stench volatiles form biological substrates. At best, metals represent a means of immediate reduction in stench, though for only short durations, and by no means cause complete stench elimination. Metals cannot act against any stench vapors per se but seem to act to temporarily and partially block some borderline reactions, mostly with nitrogen moieties, which are occurring continuously at a point in the decomposition reaction where a portion of a solid is being released as a volatile. This almost certainly means that the metal is interfering briefly at the point source during the final decompositional breakdown of amino acids into basic ammonia and ammonia complexes. A primary interference with the ongoing evolution of volatiles is almost certainly a result of coordination of the metal and amino nitrogen and ammonia ligands being evolved. The coordination complexes formed are held by coordinate bonds until other decompositional factors overcome or replace the coordinate bond energy, at which time the volatiles are again released and the metals are complexed into more stable non-volatile complexes. To become effective in terms of playing a role in stench reduction, metals must be supported by conditions and other chemical species. The same is also true for volatile-to-volatile requirements to devolatilize stench molecules that already exist, and for reducing septicity which otherwise will continue to generate ongoing stench volatiles.

Metals can be very useful in a formulation for gaining initial rapid, short term control over freed ammonia and many, though not all, of the types of amino nitrogen complexes being generated from body wastes. The metals seem to have little influence on basic volatile groups generated containing amino sulfur or amino sulfur and nitrogens.

SUMMARY OF THE INVENTION

A composition and method for reducing odor and septicity from animal waste consisting of glyoxal is disclosed. One or more aldehydes can optionally be added to the glyoxal. The aldehydes are selected from the group consisting of benzaldehyde, glycollic aidehyde, acetaldehyde, cinnamaldehyde, salicylaldehyde, citral and propionaldehyde.

Most preferably, the aldehyde is benzaldehyde or citral. The preferred amounts are between about 0.1 percent and super saturation of glyoxal, and between about 5 percent and about 10 percent benzaldehyde and/or citral. The most preferred amounts are about 40 percent glyoxal and about 10 percent benzaldehyde and/or citral.

One or more ketones can optionally be added to the glyoxal. The ketones are selected from the group consisting of diacetyl, ionone, acetylacetone, 3-buten-2-one, mesityl oxide, acetone, methyl ethyl ketone, diethyl ketone, pseudoionone, methyl nonyl ketone, ethyl octyl ketone, propyl heptyl ketone, butyl hexyl ketone, diamyl ketone, acetophenone, benzophenone and dipropyl ketone.

A surfactant can be added to the composition. The surfactant is selected from the group consisting of cationic surfactants, non-ionic surfactants, amphoteric surfactants, anionic surfactants, and zwitterionic surfactants.

A metal can be added to the composition. The metal is selected from the group consisting of zinc, copper, aluminum, iron, molybdenum, silver, boron, zirconium, salts thereof, chelates thereof, zeolites thereof, oxides thereof, carbonates thereof, hydroxides thereof, hydrates thereof, and Bordeaux mixtures thereof.

DETAILED DESCRIPTION OF THE PREFERRED EMBODIMENTS

I. OVERVIEW

In treatment of body wastes, replacement of formaldehyde and glutaraldehyde with glyoxal as a primary treatment agent resolves virtually all of the problems referred to hereinabove related to the use of those aldehydes.

Glyoxal (ethanedial, biformyl; diformyl; oxaldehyde, $C_2H_2O_2$) demonstrates very low toxicity and low to no vapor at typical ambient conditions. Glyoxal is an oxidation product of acetaldehyde. Glyoxal demonstrates a very low toxicity, even upon ingestion, and demonstrates virtually no fumes or toxic vapors under normal ambient conditions, such as within typical practical conditions encountered for treatment of body wastes. Upon ingestion, glyoxal is approximately 1,000 times less toxic to test animals than formaldehyde, and on the order of 300 times less toxic on ingestion or skin contact to test animals than glutaraldehyde.

When added to septic sewage wastes, glyoxal is equally as effective in reduction of septicity, and is, surprisingly, superior to either formaldehyde or glutaraldehyde in stench reduction. Unlike the use of either formaldehyde or glutaraldehyde for body waste treatment, body waste cannot be over-treated with glyoxal to a point where an excess will result in placing workers and users at risk under work and use conditions. Furthermore, glyoxal is considerably less corrosive with metals than either formaldehyde or glutaraldehyde.

The toxicity of glyoxal to bacteria was investigated with two cell multiplication-inhibition tests on *Pseudomonas putida*, giving an average effective concentration of $EC_{50}=$ 52 mg/l after 18 hours' exposure (mean of 46 mg/l and 57 mg/l). The effective concentrations refer to the pure substance. The experiments were carried out with a 40% dilution in water.

Furthermore, using a modified Warburg test, no inhibition of the respiration of activated sludge by a 40% dilution in water could be observed (maximum concentration 2,000 mg/l).

The data shown above indicates that formaldehyde has a higher bactericidal potential than glyoxal. However, formaldehyde is much more toxic to many aquatic invertebrates. The $EC_{50}$ values for Daphnia, for example, are about 10 times lower than for glyoxal. More drastic effects were achieved by investigating green algae (*Scenedesmus*). In this case, the toxicity of formaldehyde is about 100 times higher.

Regarding the impact of these two aldehydes on the environment, formaldehyde should only be used as a bactericidal agent if exposure to man and/or environment is excluded. If this cannot be assured, the glyoxal should be used, despite its lower bactericidal potential. Additionally, it should be taken into account that formaldehyde is a presumed carcinogen.

II. GLYOXAL ALONE FOR CONTROL OF STENCH AND SEPTICITY

EXAMPLE #1

200 mls. of 7% solids raw sewage 72 hours old was placed in a 1,000 ml. beaker covered with teflon plate. The reagents were added with a pipette to the beaker. A magnastir 1" stir bar at medium revolutions was used during reagent addition. Odor reduction was measured at 1, 2, 8 and 48 hours after treatment. The average stench level was measured by an eight-person odor panel. A scale of 0 to 10,000 stench units intensity and unpleasantness was used. Biochemical oxygen demand (BOD), the quantity of dissolved oxygen consumed in mg/l by aerobic fermentation of the sample over five days, was also measured.

| PRODUCT | A-MOUNT | STENCH UNITS BEFORE | AFTER | RESIDUAL | BOD |
|---|---|---|---|---|---|
| Formaldehyde | 10 mls. | 9,500 | 1 hr. | 2,500 | 70 PPM |
| (40% Solution) | | 9,500 | 2 hrs. | 2,000 | 56 PPM |
| | | 9,500 | 8 hrs. | 2,500 | 65 PPM |
| | | 9,500 | 48 hrs. | 2,500 | 72 PPM |
| Glutaraldehyde | 10 mls. | 9,500 | 1 hr. | 2,500 | 69 PPM |
| (40% solution) | | 9,500 | 2 hrs. | 2,500 | 71 PPM |
| | | 9,500 | 8 hrs. | 2,500 | 66 PPM |
| | | 9,500 | 48 hrs. | 3,000 | 81 PPM |
| Glyoxal | 10 mls. | 9,500 | 1 hr. | 3,000 | 82 PPM |
| (40% solution) | | 9,500 | 2 hrs. | 2,500 | 67 PPM |
| | | 9,500 | 8 hrs. | 2,000 | 54 PPM |
| | | 9,500 | 48 hrs. | 2,500 | 69 PPM |

While a 40% solution of glyoxal was employed, a glyoxal solution between about 0.10% and super saturation is within the scope of the invention. Of course, dried, supported and adducted glyoxal ranging from extremely small concentrations to the maximum obtainable can be used.

III. ADDITION OF BENZALDEHYDE

EXAMPLE #2

Addition to glyoxal of 10% benzaldehyde yielded the following results:

| PRODUCT | A-MOUNT | STENCH UNITS BEFORE | AFTER | RESIDUAL | BOD |
|---|---|---|---|---|---|
| Glyoxal | 10 mls. | 9,500 | 1 hr. | 2,000 | 59 PPM |
| (40% solution) | | 9,500 | 2 hrs. | 2,000 | 53 PPM |
| and | | 9,500 | 8 hrs. | 1,500 | 47 PPM |
| benzaldehyde | | 9,500 | 48 hrs. | 2,000 | 59 PPM |
| (10% solution) | | | | | |

Benzaldehyde added to glyoxal improves the ability to penetrate body waste masses, thereby improving the overall efficacy of stench and septicity reduction. Additionally, benzaldehyde in conjunction with glyoxal insures high effectiveness by preventing auto-polymerization of the glyoxal, thereby preserving it in the more reactive monomeric form. Glyoxal would otherwise automatically become less effective if applied alone as an aqueous solution, or upon addition to body wastes or manure suspended in an aqueous solution.

IV. ADDITION OF ALDEHYDES AND KETONES GENERALLY

EXAMPLE #3

Addition of citral, cinnamaldehyde, crotonaldehyde, benzaldehyde, propionaldehyde, glycollic aldehyde, acetaldehyde and salicylaldehyde to glyoxal also aids in reduction of stench and septicity.

Addition of ketones such as diacetyl, ionone, acetylacetone, 3-buten-2-one, mesityl oxide, acetone, methyl ethyl ketone, diethyl ketone, pseudoionone, methyl nonyl ketone, ethyl octyl ketone, propyl heptyl ketone, butyl hexyl ketone, diamyl ketone, acetophenone, benzophenone and dipropyl ketone in place of aldehydes were comparable to benzaldehyde added to glyoxal. Volatiles distinct to the particular ketone were noticeable as background volatiles. Except when pleasant aroma and improved solvency are critical, ketones are generally more effective when used as sulfite adducts of aldehydes and ketones, or ketones.

| PRODUCT | A-MOUNT | STENCH UNITS BEFORE | AFTER | RESIDUAL | BOD |
|---|---|---|---|---|---|
| Glyoxal | 10 mls. | 9,500 | 1 hr. | 2,500 | 70 PPM |
| (40% solution) | | 9,500 | 2 hrs. | 2,000 | 52 PPM |
| and citral | | 9,500 | 8 hrs. | 1,500 | 39 PPM |
| (10% solution) | | 9,500 | 48 hrs. | 2,000 | 54 PPM |

While a 40% solution of glyoxal was employed, a glyoxal solution between about 0.10% and super saturation is within the scope of the invention. Of course, dried, supported and adducted glyoxal ranging from extremely small concentrations to the maximum obtainable can be used.

V. ADDITION OF METALS AND SURFACTANTS

EXAMPLE #4

| PRODUCT | A-MOUNT | STENCH UNITS BEFORE | AFTER | RESIDUAL | BOD |
|---|---|---|---|---|---|
| Glyoxal | 10 mls. | 9,500 | 1 hr. | 2,000 | 66 PPM |
| (40% solution) | 10 mls. | 9,500 | 2 hrs. | 2,000 | 64 PPM |
| and quaternary | 10 mls. | 9,500 | 8 hrs. | 2,000 | 45 PPM |
| "Quat 10" | 10 mls. | 9,500 | 48 hrs. | 2,000 | 47 PPM |
| (10% solution) | | | | | |
| Glyoxal | 10 mls. | 9,500 | 1 hr. | 1,000 | 48 PPM |
| (40% solution) | 10 mls | 9,500 | 2 hrs. | 1,000 | 39 PPM |
| and saturated | 10 mls. | 9,500 | 8 hrs. | 500 | 30 PPM |
| solution | 10 mls. | 9,500 | 48 hrs. | 1,000 | 41 PPM |
| copper sulfate | | | | | |
| (10% solution) | | | | | |

While a 40% solution of glyoxal was employed, a glyoxal solution between about 0.10% and super saturation is within the scope of the invention. Of course, dried, supported and adducted glyoxal ranging from extremely small concentrations to the maximum obtainable can be used.

Copper replacement with zinc chloride or sulfate yielded the same results as above. The addition of iron sulfate or aluminum sulfate was comparable to glyoxal and quat 10. Silver nitrite was less effective for stench reduction but more effective for reduction of septicity, and the effects lasted longer.

EXAMPLE #5

Addition to glyoxal of a 10% saturated solution of copper and a 5% solution of cationic surfactant follows:

| PRODUCT | A-MOUNT | STENCH UNITS BEFORE | AFTER | RESI-DUAL | BOD |
|---|---|---|---|---|---|
| Glyoxal | 10 mls. | 9,500 | 1 hr. | <100 | 30 PPM |
| (40% solution) | | 9,500 | 2 hrs. | <500 | 27 PPM |
| and sat. solution | | 9,500 | 8 hrs. | <500 | 30 PPM |
| copper sulfate | | 9,500 | 48 hrs. | 500 | 33 PPM |
| (10% solution) | | | | | |
| and sat. solution | | | | | |
| cat. surfactant | | | | | |
| (5% solution) | | | | | |

While a 40% solution of glyoxal was employed, a glyoxal solution between about 0.10% and super saturation is within the scope of the invention. Of course, dried, supported and adducted glyoxal ranging from extremely small concentrations to the maximum obtainable can be used.

Surfactants are selected from, in order of preference, cationic, nonionic, anionic, amphoteric and zwitterionc. The most preferred cationic surfactant contains at least one halogen, most preferably bromine.

VI. MULTIPLE ADDITIONS OF ALDEHYDES, KETONES, SURFACTANTS AND METALS

EXAMPLE #6

A formula comprised of the following ingredients is effective for the reduction of stench and septicity:

| ALLOWED | RANGE (%) | PREFERRED RANGE |
|---|---|---|
| One or more aldehydes | 0.1–100 | 30–90 |
| One or more ketones | 0–100 | 1–50 |
| One or more surfactants | 0–90 | 5–35 |
| One or more metals | 0–90 | 5–35 |

Where a single aldehyde is used, benzaldehyde is acceptable, but glyoxal is preferred.

Plural aldehydes may be selected from, in order of preference: glyoxal, benzaldehyde, citral, cinnamaldehyde, crotonaldehyde, propionaldehyde, acetaldehyde, and salicylaldehyde.

Ketones are selected from, in order of preference, 2,3-butanedione (diacetyl), $\alpha$ and $\beta$ ionone, acetylacetone, 3-buten-2-one, mesityl oxide, acetone, methyl ethyl ketone, diethyl ketone, pseudoionone, methyl nonyl ketone, ethyl octyl ketone, propyl heptyl ketone, butyl hexyl ketone, diamyl ketone, acetophenone, and benzophenone. Except when pleasant aroma and improved solvency are critical, ketones are generally more effective when used as sulfite adducts of aldehydes and ketones, or ketones.

Surfactants are selected from, in order of preference, cationic, nonionic, anionic, amphoteric and zwitterionc. The most preferred cationic surfactant contains at least one halogen, most preferably bromine.

Metals are selected from transition metals (excluding chromium, nickel, and cadmium) and non-transition elements of boron and aluminum. For single metal additions, copper, zinc, silver, zirconium and boron are preferred. For plural metals additions, copper, zinc, iron, aluminum and molybdenum are preferred in their different combinations. The most preferred combinations include at least one non-amphoteric metal, such as copper or iron, in combination with at least one amphoteric metal, such as aluminum or zinc. Preferred forms of water soluble metal salts are, in order of preference: sulfates, chloride, oxides, and acetates. Preferred non-soluble forms are bordeaux-type salts, such as those formed from calcium hydroxide, slaked lime, copper, zinc, iron and the like.

VII. USE IN PORTABLE WASTE CONTAINMENT SYSTEMS

Portable waste containment systems or restrooms are widely utilized at remote work and other locations. Construction sites, large temporary gatherings and high traffic areas which, for one reason or another, do not have available sewage services.

Portable restrooms may be constructed of a variety of materials, among which preformed fiberglass is typical. These units are designed to be readily portable and are moved onto a site for use for a specified period of time by an estimated number of persons. A typical unit is totally enclosed with adequate inner space to accommodate one person. The unit typically contains a holding reservoir which is pre-loaded with an amount of water deemed to give adequate liquid to dilute incoming waste sufficient to allow body wastes to be diluted for more compact storage and to permit some aqueous solvent for added treating agents. Formaldehyde is a typical treating agent. The water contained in the reservoir may range anywhere from several to as much as twenty gallons. A typical formaldehyde treatment may be from 2 to 16 or more ounces of 36% solution. Many proprietary products are available which also include dyes and other ingredients to aid in stench and septic control.

EXAMPLE #7

A portable toilet constructed of fiberglass with a five-gallon treating agent reservoir was treated with five gallons of water to which the following were added:

| | A-MOUNT | RESI-DUAL VOLA-TILES | STENCH REDUC-TION | PRO-DUCT CHAR-ACTER |
|---|---|---|---|---|
| TEST 1 | | | | |
| Formaldehyde (40% solution) | 5 ozs. | Yes, Strong form-aldehyde | ~70%, Moderate, sweet, stinging after-odor | Strong, irritating, choking odor |
| TEST 2 | | | | |
| Glutaraldehyde (40% Solution) | 5 oz. | Yes, Moderate glutar-aldehyde | ~70%, Moderate chemical after-odor | Moderately unpleasant chemical odor |
| TEST 3 | | | | |
| Glyoxal (40% solution) | 5 ozs. | None | ~70% Good | No odor |

While a 40% solution of glyoxal was employed, a glyoxal solution between about 0.10% and super saturation is within the scope of the invention. Of course, dried, supported and adducted glyoxal ranging from extremely small concentrations to the maximum obtainable can be used.

The tests were conducted after three days' use by six persons. Results were confirmed by use of 100 grams of activated carbon. After three days the carbon was collected and covered with 200 grams of ethanol and distilled through a distillation column. Samples of the distillate were injected into a Hewlett Packard Model H.P. 1A gas chromatograph, using a Supelcoport 10-inch/18-inch column (10° SP-2100, 100/120) across a flame ionization detector.

| Results: | TEST 1: | Formaldehyde | 177 PPM |
|---|---|---|---|
| | TEST 2: | Glutaraldehyde | 96 PPM |
| | TEST 3: | Glyoxal | None |

BOD samples were taken of raw sewage from reservoir.

| | | BEFORE | AFTER |
|---|---|---|---|
| Results: | TEST 1: | 155 PPM | 45 PPM |
| | TEST 2: | 165 PPM | 49 PPM |
| | TEST 3: | 149 PPM | 41 PPM |

Five ounces of the following added under same conditions above:

| | A-MOUNT | RESIDUAL VOLATILES | STENCH REDUCTION | PRODUCT CHARACTER |
|---|---|---|---|---|
| TEST 4: | | | | |
| Water | 55% | None | ~80–90%, Excellent | Slight odor |
| Glyoxal | 35% | | | |
| Benzaldehyde | 10% | | | |
| TEST 5: | | | | |
| Water | 55% | None | ~80–90%, Excellent | Faint odor |
| Glyoxal | 35% | | | |
| Quat 10 | 10% | | | |
| TEST 6: | | | | |
| Water | 55% | None | ~90%, Excellent | None |
| Glyoxal | 35% | | | |
| Zinc chloride | 10% | | | |
| TEST 7: | | | | |
| Water | 55% | None | ~80–90%, Excellent | Slight odor |
| Glyoxal | 35% | | | |
| Benzaldehyde | 5% | | | |
| Methyl nonyl ketone | 5% | | | |
| TEST 8: | | | | |
| Water | 54% | None | ~90–99%, Excellent | Slight pleasant odor |
| Glyoxal | 34% | | | |
| Benzaldehyde | 4% | | | |
| Methyl nonyl ketone | 4% | | | |
| Copper sulfate | 4% | | | |
| TEST 9: | | | | |
| Water | 52% | None | ~90–99%, Excellent | Slight pleasant odor |
| Glyoxal | 32% | | | |
| Benzaldehyde | 4% | | | |
| Methyl nonyl ketone | 2% | | | |
| Copper sulfate | 4% | | | |
| "BARLOX" (N-alkyl-N, N-dimethyl-amine oxide) | 6% | | | |

| | A-MOUNT | RESIDUAL VOLATILES | STENCH REDUCTION | PRODUCT CHARACTER |
|---|---|---|---|---|
| TEST 10: | | | | |
| Water | 52% | None | ~99–100%, Excellent | Slight pleasant odor |
| Glyoxal | 31% | | | |
| Benzaldehyde | 3% | | | |
| Methyl nonyl ketone | 2% | | | |
| Copper sulfate | 4% | | | |
| Silver nitrate | 2% | | | |
| "BARLOX" | 6% | | | |
| TEST 11: | | | | |
| Water | 21% | None | 100%, Excellent | Slight pleasant odor |
| "BARLOX" | 24% | | | |
| Glyoxal | 25% | | | |
| Copper sulfate | 15% | | | |
| Benzaldehyde | 1% | | | |
| Citric acid | 7% | | | |
| "PINE-SOL" | 2% | | | |
| VanWet 9N9 | 5% | | | |

This last formula reduced stench much faster than other formulations. Septicity was improved, as measured by BOD, from 100 ppm down to 3 ppm after only 30 minutes. The effects were also longer lasting; the BOD still only measuring 18 ppm after one week.

VIII. USE IN AIRLINE, MARINE AND RECREATIONAL VEHICLE

WASTE CONTAINMENT SYSTEMS

Airline, marine and recreational vehicle waste containment systems are generally comprised in part of aluminum alloys which are employed for their light weight and high strength-to-weight ratio. Aluminum alloys pose a unique problem in that many chemicals employed in waste containment corrode these alloys. The following example provides an exemplary chemical composition of the present invention which does not corrode aluminum alloys.

EXAMPLE #8

| FORMULA | A-MOUNT | RESIDUAL VOLATILES | STENCH REDUCTION | PRODUCT CHARACTER |
|---|---|---|---|---|
| Quat 10 | 6% | NONE | 100% Excellent | Slight pleasant odor |
| Glyoxal (40%) | 62% | | | |
| Buffered zinc—(copper/zinc Bordeaux solution) | 11% | | | |
| Benzaldehyde | 2% | | | |
| Ethyl alcohol | 5% | | | |
| Pseudoionone | 1% | | | |
| VanWet 9N9 | 5% | | | |

While a 40% solution of glyoxal was employed, a glyoxa solution between about 0.10% and super saturation is within the scope of the invention. Of course, dried, supported and adducted glyoxal ranging from extremely small concentrations to the maximum obtainable can be used.

The copper or zinc in Bordeaux mix may be replaced by chelated copper or zinc sulfate, chloride, acetate or other salts. Chelation may be with EDTA, or other effective chelates, and/or with synergists such as citric, oxalic, phosphoric or other organic acids, or alkaline earth metal salts thereof, such as sodium citrate. The metal salts may be buffered to between 6 and 8.5. Zinc is preferred for this formulation, whether in the buffered or chelated form, and can be used in the range of from about 5 to 15%. When a direct replacement for the bordeaux complex, 11% is the preferred amount.

This formulation was at least equivalent in performance for stench reduction with Test 11 above. BOD reductions were equivalent also. When contact tested for corrosiveness against alloyed aircraft aluminum samples, the metal exposed to the product of Example 8 showed no significant pitting after 2 weeks.

Current formulations used in many passenger aircraft holding tanks contain formaldehyde, paraformaldehyde or glutaraldehyde. The presence of such additives represents a hazard to passengers, maintenance crews and crew members. With the above formulations, the hazards are greatly reduced, and effectiveness is superior to those formulations currently in use. The hazards are reduced not only with respect to markedly decreased toxicity in the event of contact from handling or a spill, but also the release of toxic fumes from such additives currently in use is avoided entirely.

While particular embodiments of the present invention have been described in some detail herein above, changes and modifications may be made in the illustrated embodiments without departing from the spirit of the invention.

I claim:

1. An antibacterial composition for reducing stench from animal waste consisting of:

glyoxal;

benzaldehyde; and a metal selected from the group consisting of zinc, copper, aluminum, iron, molybdenum, silver, boron, zirconium, salts thereof, chelates thereof, zeolites thereof, oxides thereof, carbonates thereof, hydroxides thereof, hydrates thereof, sulfates thereof, chlorides thereof, and nitrates thereof.

2. An antibacterial composition for reducing stench from animal waste consisting of:

glyoxal;

a metal compound, said metal of said metal compound being selected from the group consisting of zinc, copper, aluminum, iron, molybdenum, titanium, silver, boron and zirconium;

benzaldehyde;

ethyl alcohol;

pseudoionone;

and quaternary ammonium.

3. An antibacterial composition for reducing stench from animal waste consisting of:

between about 10 weight percent and about 90 weight percent glyoxal;

between about 10 weight percent and about 50 weight percent benzaldehyde; and between about 5 weight percent and about 35 weight percent of a metal selected from the group consisting of zinc, copper, aluminum, iron, molybdenum, silver, boron, zirconium, salts thereof, chelates thereof, zeolites thereof, oxides thereof, carbonates thereof, hydroxides thereof, hydrates thereof, sulfates thereof, chlorides thereof, and nitrates thereof.

* * * * *